(12) United States Patent
Sun et al.

(10) Patent No.: US 6,447,731 B1
(45) Date of Patent: Sep. 10, 2002

(54) CLEANING DEVICE

(76) Inventors: Shin-Ching Sun, P.O. Box 24-108, Taipei (TW); Hubert Chou, P.O. Box 24-108, Taipei (TW)

( * ) Notice: Subject to any disclaimer, the term of this patent is extended or adjusted under 35 U.S.C. 154(b) by 251 days.

(21) Appl. No.: 09/606,127

(22) Filed: Jun. 28, 2000

(51) Int. Cl.7 .................................................. A62B 7/08
(52) U.S. Cl. .................. 422/121; 422/122; 422/186.07; 55/210; 96/58
(58) Field of Search ............................ 422/121, 5, 122, 422/186.3, 186.07, 169; 55/210; 96/57, 58, 59

(56) References Cited

U.S. PATENT DOCUMENTS

| | | | |
|---|---|---|---|
| 4,792,345 A | * 12/1988 | Abe et al. ...................... | 55/210 |
| 5,622,543 A | * 4/1997 | Yang .............................. | 96/58 |
| 5,681,533 A | * 10/1997 | Hiromi ........................ | 422/121 |

FOREIGN PATENT DOCUMENTS

JP          09079612 A    *  3/1997

* cited by examiner

*Primary Examiner*—Robert J. Warden, Sr.
*Assistant Examiner*—Sean E. Conley

(57) ABSTRACT

A cleaning device including a sensor, a circuit board, a fan motor, an optical catalyst glass fiber filter mesh, an anion and ozone generator and a power supply. The cleaning device is able to collect dust and remove odor. Also, the cleaning device is able to generate ozone and natural anion to activate human cells and help in blood circulation. In addition, by means of a USB (Universal Serial Bus) signal cable or IBM PS/2 signal cable, the cleaning device can be connected to a personal computer to serve as a peripheral equipment of the computer and form an environmental quality monitoring system. The computer can show the air quality index of the environment. The index can be presented through image or sound of the computer.

8 Claims, 5 Drawing Sheets

CLEANING DEVICE

BACKGROUND OF THE INVENTION

The present invention relates to a cleaning device which can be connected with a personal computer to serve as an environmental quality monitoring system which is able to automatically judge and adjust indoor air quality, and give more information for a user. It is established in the personal computer as for new peripheral equipment.

A conventional air cleaning device utilizes ionized electrode and dust-collecting electrode to discharge and ionize suspending particles in the air, such as dust, micro-particle, virus, pollen, excretion of louse, etc. These ionized particles are attracted to move toward the dust-collecting electrode and finally attach to a dust-collecting paper positioned in front of the dust-collecting electrode.

Such air cleaning device is able to remove the dust. However, it is impossible for such air cleaning device to detect a proper using time and display relative information. That is, when a smoker smokes or a food with special odor is brought into a room, the cleaning device must be activated by the user himself to filter off the odor and particles in the air. In the case that micro-particles which can be hardly perceived are entrained in the air and a user fails to activate the air cleaning device, the health of the user may be harmed.

SUMMARY OF THE INVENTION

It is therefore a primary object of the present invention to provide a cleaning device which is able to collect dust and remove odor. Also, the cleaning device is able to generate ozone and natural anion to activate human cells and help in blood circulation.

It is a further object of the present invention to provide the above cleaning device which can be connected with a computer and controlled by computer program to serve as an environmental quality monitoring system. Relevant information with respect to the environment such as image and sound can be shown via the personal computer monitor and speaker.

According to the above objects, the cleaning device of the present invention is composed of a sensor, a circuit board, a fan motor, an air filter mesh, an anion and ozone generator and a power supply. The cleaning device is able to collect dust and remove odor. Also, the cleaning device is able to generate ozone and natural anion to activate human cells and help in blood circulation. In addition, by means of a USB signal cable or IBM PS/2 signal cable, the cleaning device can be connected to a computer and controlled by computer program. The relevant environmental information such as image and sound can be shown via the personal computer monitor and speaker to form an environmental quality monitoring system. The device includes the necessary transceiver for USB (Universal Serial Bus) or IBM PS/2 operation and meets all of the active and standby current specifications for new peripheral device.

The present invention can be best understood through the following description and accompanying drawings wherein:

DETAILED DESCRIPTION OF THE PREFERRED EMBODIMENTS

Figure 1:
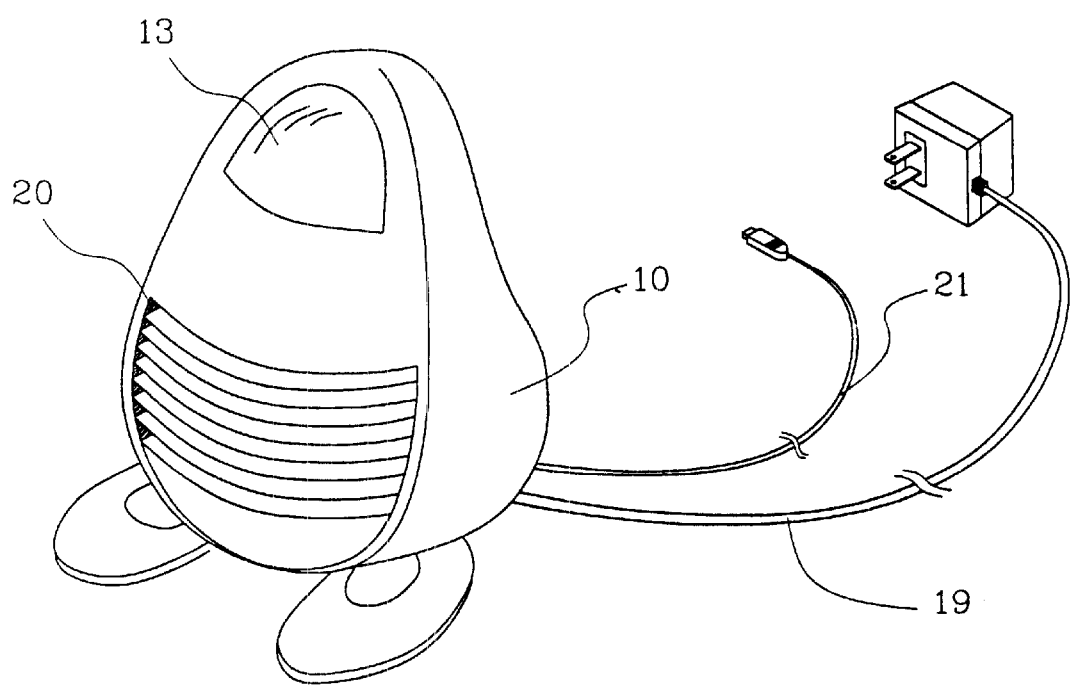
FIG. 1 is a perspective view of an embodiment of the present invention.
Figure 2:
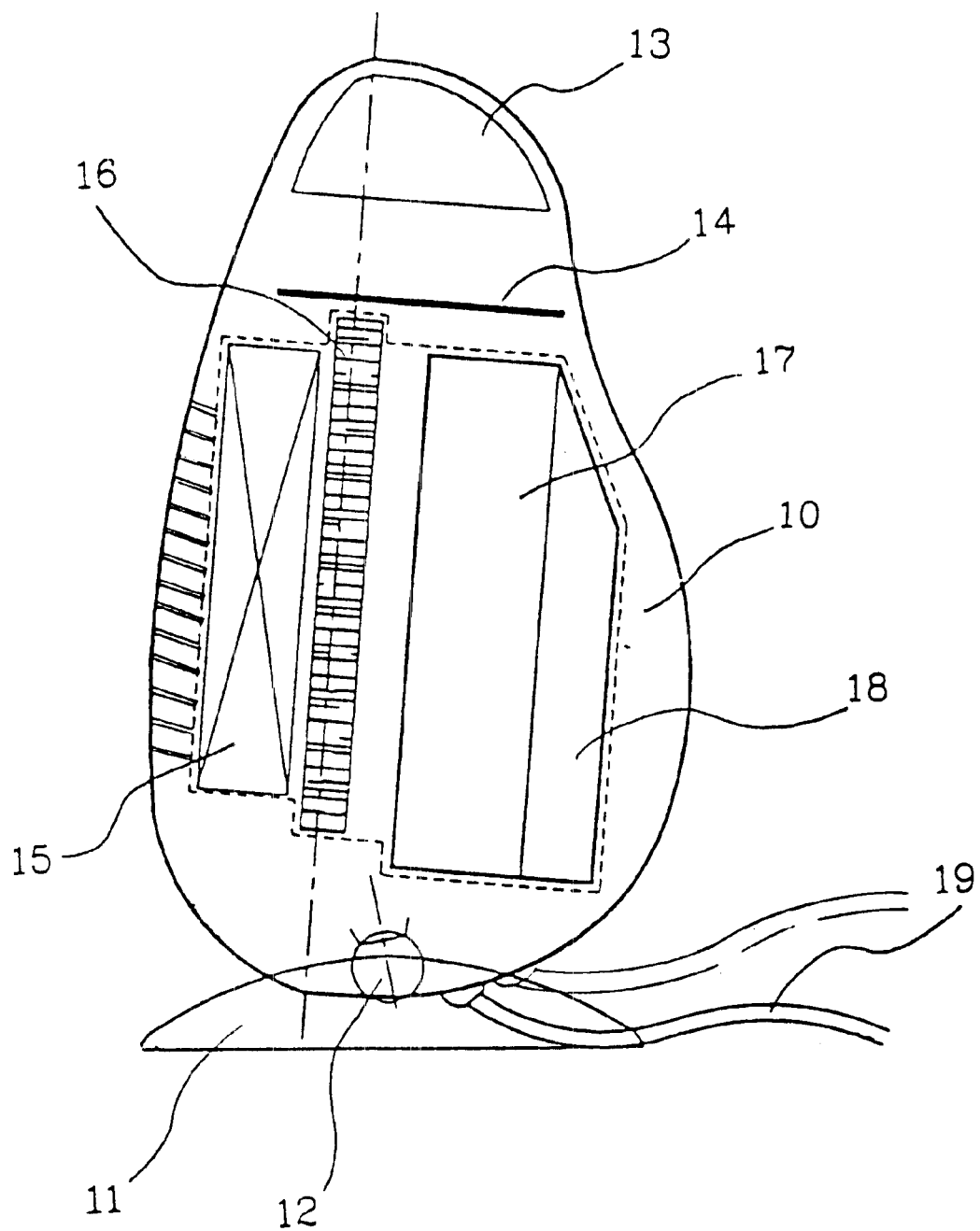
FIG. 2 is a sectional view of the first embodiment of the present invention.

Please refer to FIGS. 1 and 2. The present invention has a substantially elliptic housing 10 formed with ventilation vents 20. Two sides of the bottom of the housing 10 are respectively disposed with two spherical joints 12 for connecting with two semielliptic bases 11. In the housing 10 are installed a sensor 13, a circuit board 14, a fan motor 15, an optical catalyst glass fiber cloth 16, an anion and ozone generator 17 and a power supply 18. A power cable 19 and a USB signal cable 21 (or IBM PS/2 signal cable) extend out of the housing 10.

A coating of titanium dioxide ($TiO_2$) is plated on the optical catalyst glass fiber cloth 16. The titanium dioxide coating acts with the ultraviolet light of sunlight or illuminator (wave length<400 nm). After the titanium dioxide absorbs ultraviolet light, two kinds of carriers of electron and electric hole are produced to respectively create oxidation and reduction reaction and thus achieve bactericidal, pollutionproof and deodoring (air purifying) effect.

After the power cable 19 is plugged into a socket, the power supply 18 provides power for respective components. The circuit board 14 generally controls the sensor 13, fan motor 15 and anion and ozone generator 17. The sensor 13 includes an ultraviolet sensor and VOC (Volatile Organic Compound) sensor. The ultraviolet sensor serves to detect instantaneous flame of a lighter (effective range 1.5 M semicircumference, transmitting high/low single signal). The VOC sensor serves to transmit high/low single signal of 1 k~10 kHz frequency to a microcontroller on the circuit board 14 according to the contamination extent. The anion and ozone generator 17 controls and generates anion and ozone, depending on the strength of the signal. According to the air contamination extent detected by the sensor 13, the circuit board 14 automatically selects the operation modes (fast/standard/silent) of the fan motor 15. The dirty air goes into the ventilation vents 20 and passes through the optical catalyst glass fiber filter mesh 16 so as to filter off the suspending particle, oil smoke and odor in the air.

Figure 3:
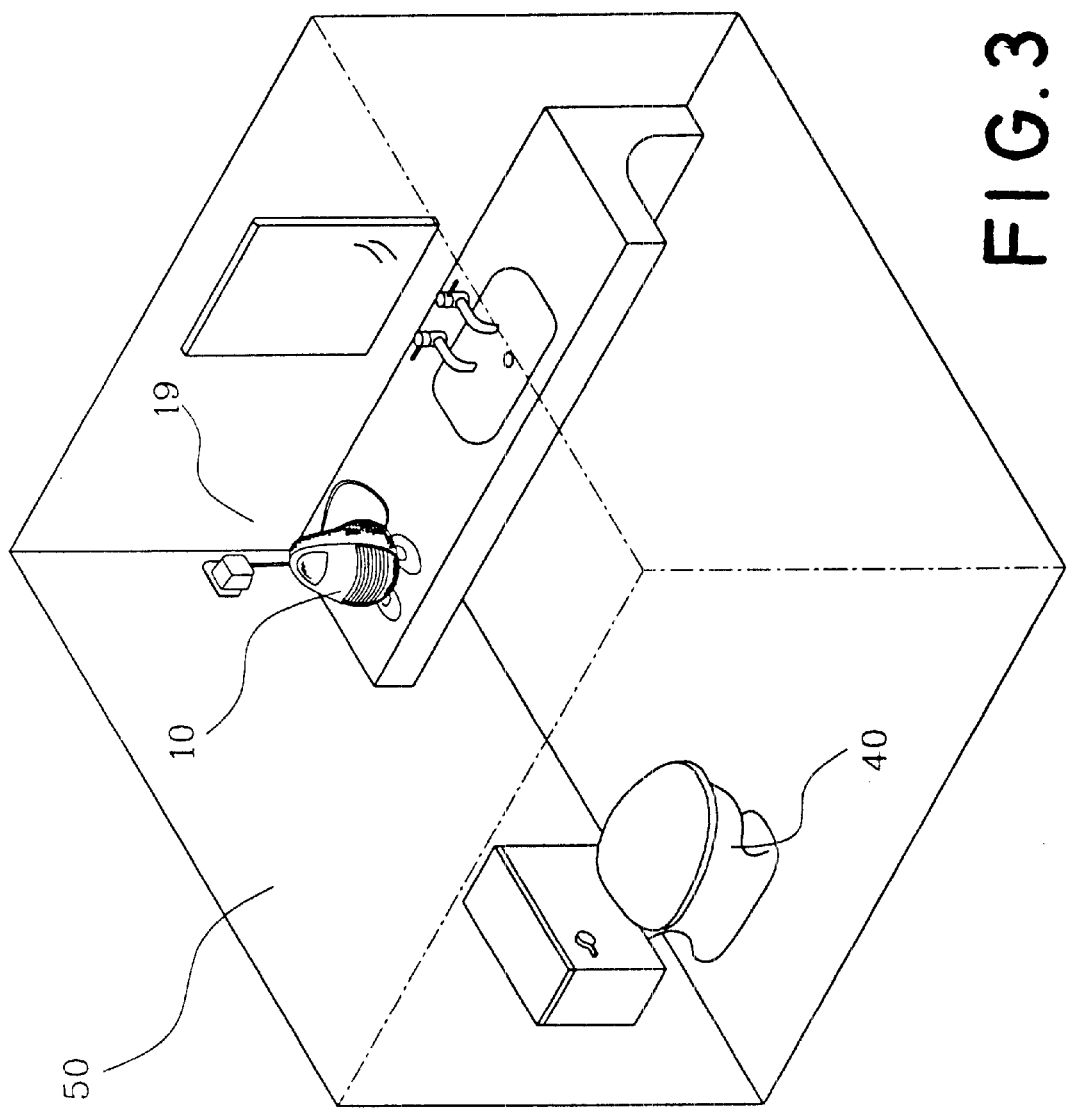
FIG. 3 shows an application of the present invention to a toilet.

As shown in FIG. 3, the present invention can be placed in a toilet 50. After a user uses the toilet bowl 40, the VOC sensor of the sensor 13 detects the odor and the circuit board 14 according to the contamination extent detected by the VOC sensor activates the fan motor 15 and automatically selects a suitable operation mode. Also, the anion and ozone generator 17 generates anion and makes the contaminated air in the toilet 50 filtered, dust-collected and deodored by the optical catalyst glass fiber filter mesh 16 and then purified by the anion so as to achieve a clean and fresh air. Furthermore, in the case of smoking in a close space, the ultroviolet sensor of the sensor 13 will detect the flame and the VOC sensor will detect the smoke (Volatile Organic Compound). At this time, the present invention will repeat the above operation to freshen the air in the close space.

Figure 4:
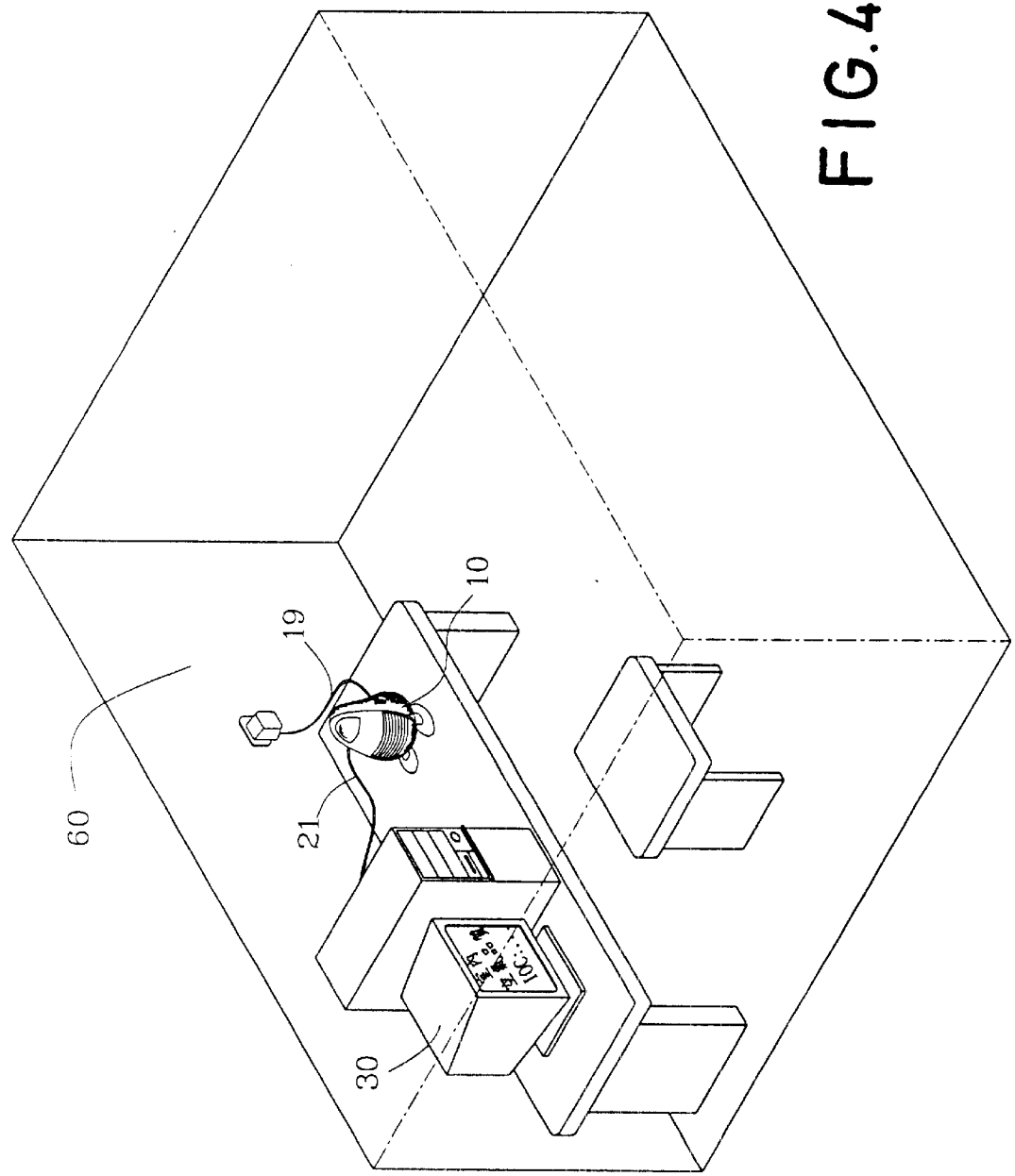
FIG. 4 shows that the present invention is connected with a computer.

The USB signal cable 21 (or IBM PS/2 signal cable) of the present invention can be connected to a personal computer 30 (as shown in FIG. 4). Therefore, the cleaning device can be controlled by computer program and relevant information such as image and sound can be shown via the computer monitor. Accordingly, a user in the close space 60 can clearly know the quality index of the environmental air in the space and record the variation value for a long term so as to suggest a measure of treatment and improvement. Therefore, an environmental air quality monitoring system can be established.

Figure 5:
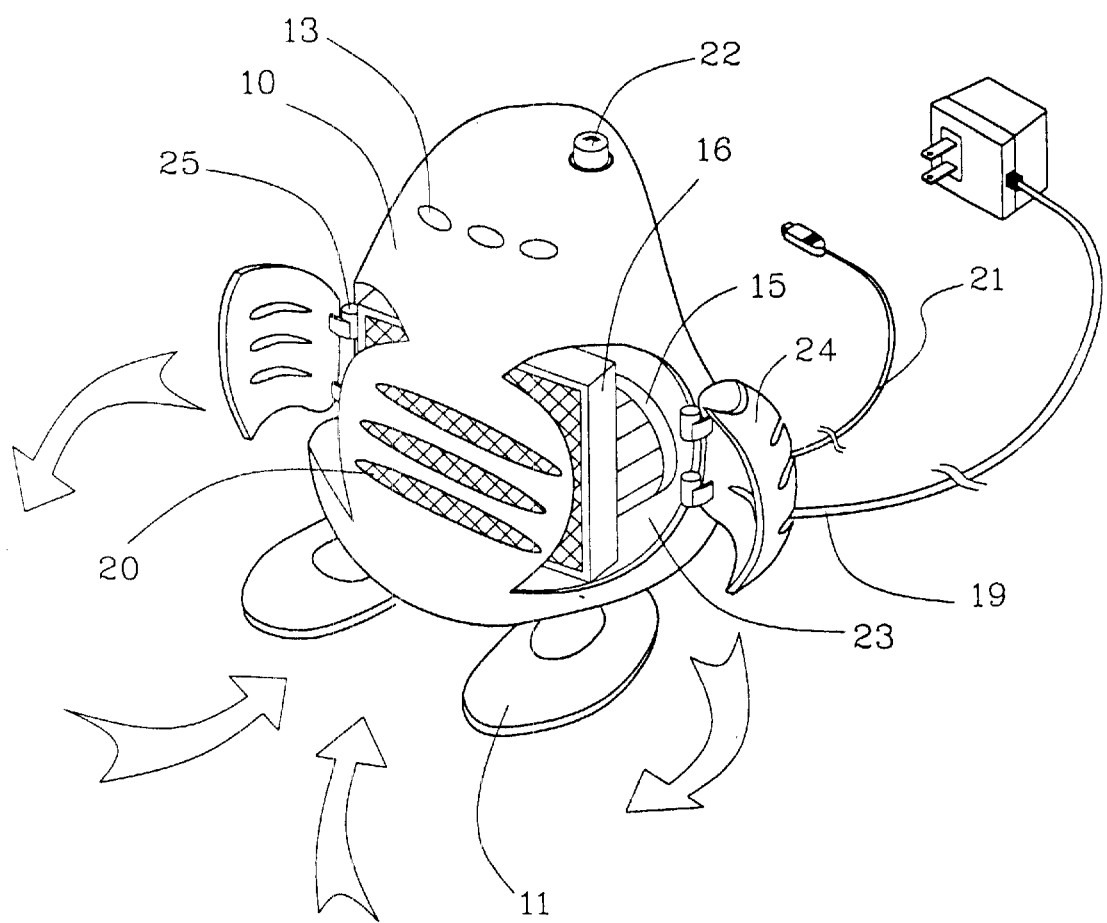
FIG. 5 is a perspective view of another embodiment of the present invention.

In addition, FIG. 5 shows another embodiment of the present invention, in which the top is disposed with a switch 22. Two sides of the ventilation vents 20 are respectively disposed two substantially crescent wing recess 23. A shaft pin 25 is disposed on one side of the wing recess 23 for pivotally connecting with a wind-guiding wing 24. In use, the wing 24 is opened and the air is sucked into the ventilation vents 20 to filter through the optical catalyst glass fiber cloth 16 and anion and ozone generator 17. Thereafter, the fresh air is guided by the two lateral wind-guiding wings 24 out of the cleaning device to create a circulation and convection. Therefore, the harmful air is quickly and effectively eliminated. According to the above arrangement, the cleaning device of the present invention by means of the USB signal cable can be connected to a computer to serve as a peripheral equipment of the computer and form an environmental quality monitoring system.

The above embodiments are only used to illustrate the present invention, not intended to limit the scope thereof. Many modifications of the above embodiments can be made without departing from the spirit of the present invention.

What is claimed is:

1. A cleaning device comprising a sensor, a circuit board, a fan motor, an optical catalyst glass fiber filter mesh, an anion and ozone generator and a power supply, a housing of the cleaning device being formed with ventilation vents, two sides of a bottom of the housing being respectively disposed with two joints for connecting with two bases, in the housing being installed the sensor, the circuit board, the fan motor, the optical catalyst glass fiber filter mesh, the anion and ozone generator and the power supply, the circuit board generally controlling the respective components, a power cable and a signal cable extending out of the housing to connect with a personal computer and serve as a computer peripheral equipment.

2. A cleaning device as claimed in claim 1, wherein the sensor includes an ultraviolet sensor and a VOC (Volatile Organic Compound) sensor.

3. A cleaning device as claimed in claim 1, wherein the fan motor has three modes of fast/standard/silent which are controlled by the circuit board.

4. A cleaning device as claimed in claim 1, wherein the cleaning device can be automatically controlled by computer program.

5. A cleaning device as claimed in claim 4, wherein the computer serves as an environmental air quality monitoring system.

6. A cleaning device as claimed in claim 1, wherein a coating of titanium dioxide ($TiO_2$) is plated on an optical catalyst glass fiber cloth to form the optical catalyst glass fiber filter mesh.

7. A cleaning device as claimed in claim 1, wherein two sides of the ventilation vents of the housing are formed with wing recesses for pivotally connected with two wind-guiding wings.

8. A cleaning device as claimed in claim 7, wherein the wind-guiding wings are arched.

* * * * *